United States Patent

Kato et al.

Patent Number: 5,945,415
Date of Patent: Aug. 31, 1999

[54] (R)-5-BROMO-N-(1-ETHYL-4-METHYLHEXAHYDRO-1H-1,4-DIAZEPIN-6-YL)-2-METHOXY-6-METHYLAMINO-3-PYRIDINECARBOXAMIDE, PROCESS FOR PRODUCING THE SAME AND MEDICINAL COMPOSITION CONTAINING THE SAME

[75] Inventors: Shiro Kato, Sakai; Yoshimi Hirokawa, Ikoma; Toshiya Morie, Matsubara; Hiroshi Harada, Suita; Naoyuki Yoshida, Sakai, all of Japan

[73] Assignee: Dainippon Pharmaceutical Co., Ltd., Osaka, Japan

[21] Appl. No.: 09/000,468

[22] PCT Filed: Jul. 23, 1996

[86] PCT No.: PCT/JP96/02053

§ 371 Date: Jan. 23, 1998

§ 102(e) Date: Jan. 23, 1998

[87] PCT Pub. No.: WO97/05129

PCT Pub. Date: Feb. 13, 1997

[30] Foreign Application Priority Data

Jul. 28, 1995 [JP] Japan .................................. 7-212495

[51] Int. Cl.⁶ .......................... A61K 31/55; C07D 243/08
[52] U.S. Cl. .................................... 514/218; 540/575
[58] Field of Search ............................. 514/218; 540/575

[56] References Cited

U.S. PATENT DOCUMENTS

| 5,017,573 | 5/1991 | Kon et al. ............... 514/218 |
| 5,166,341 | 11/1992 | Kon et al. ............... 540/575 |

FOREIGN PATENT DOCUMENTS

| 0 358 903 | 3/1990 | European Pat. Off. . |
| 3-223265 | 10/1991 | Japan . |
| 4-210970 | 8/1992 | Japan . |
| 5-92959 | 4/1993 | Japan . |
| WO93/08186 | 4/1993 | WIPO . |

OTHER PUBLICATIONS

Hirokawa et al., "Synthesis and structure–activity relationships of N-(1-ethyl-4-methylhexahydro-1H-1,4-diazepin-6-yl)amides with potent dopamine $D_2$ and serotonin 5-$HT_3$ receptor antagonistic activities", AIMECS 95, AFMC International Medicinal Chemistry Symposium, Program, Abstracts and Handbook, Sep. 3–8, 1995, Tokyo, Japan.

Primary Examiner—Mukund J. Shah
Assistant Examiner—Brenda Coleman
Attorney, Agent, or Firm—Wenderoth, Lind & Ponack, L.L.P.

[57] ABSTRACT

This invention discloses a compound which is expressed by formula (I) below:

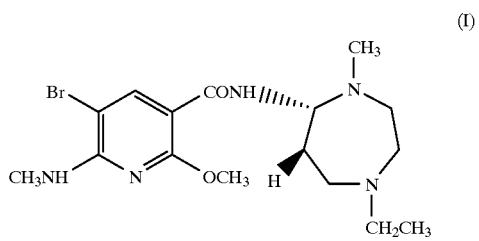

or physiologically acceptable acid addition salts thereof. The claimed compound exhibits excellent antiemetic effect based on its potent serotonin $S_3$ and dopamine $D_2$ receptor antagonistic activities, and is useful for treatment or prophylaxis of various gastrointestinal symptoms which are associated with various diseases and drug administration.

5 Claims, No Drawings

(R)-5-BROMO-N-(1-ETHYL-4-METHYLHEXAHYDRO-1H-1,4-DIAZEPIN-6-YL)-2-METHOXY-6-METHYLAMINO-3-PYRIDINECARBOXAMIDE, PROCESS FOR PRODUCING THE SAME AND MEDICINAL COMPOSITION CONTAINING THE SAME

CROSS-REFERENCE TO RELATED APPLICATION

This application is a 371 of PCT/JP96/02053, filed Jul. 23, 1996.

TECHNICAL FIELD

This invention relates to novel (R)-5-bromo-N-(1-ethyl-4-methylhexahydro-1H-1,4-diazepin-6-yl)-2-methoxy-6-methylamino-3-pyridinecarboxamide which exhibits potent serotonin $S_3$ (which may be hereafter referred to as 5-$HT_3$) and dopamine $D_2$ receptor antagonistic activities; process for preparation thereof; and pharmaceutical composition containing said compound.

BACKGROUND ART

Japanese Laid-open (KOKAI) Patent Application, KOKAI No. 92959/1993 broadly discloses a class of compounds represented by formula (A) below:

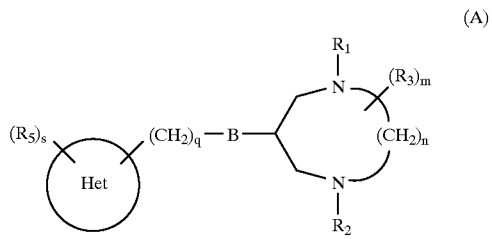

(A)

[in which $R_1$ and $R_2$ may be same or different, and each signifies hydrogen atom, lower alkyl or substituted lower alkyl group, etc.

$R_3$ may be same or different and each signifies hydrogen atom or lower alkyl, etc.

$R_5$ may be same or different and each signifies hydrogen atom, halogen atom, lower alkoxy, amino, mono- or di-substituted amino group, etc.

Het signifies a monocyclic heteroaryl or di-cyclic heteroaryl other than 1H-indazolyl group, q is 0, 1 or 2, s is 1, 2 or 3, B signifies —$CXNR_6(CH_2)_r$—, etc. in which $R_6$ signifies hydrogen atom or lower alkyl, etc.

X signifies oxygen or sulfur atom and r is 0, 1, 2 or 3, m is 1, 2, 3 or 4, and n is 1, 2 or 3], and also discloses that Het can stand for pyridyl. Whereas, a sole specific compound in which Het is 3-pyridyl group and which is disclosed in the specification is the one of Example 37, represented by the formula below:

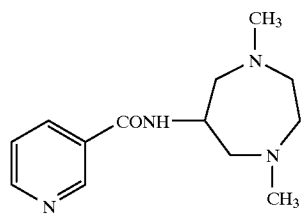

This compound of Example 37 clearly differs in structure from the compound of the present invention which is expressed by the later presented formula (I). In the former compound, 3-pyridyl group is unsubstituted and 4-position of hexahydro-1H-1,4-diazepine is substituted with methyl.

Said KOKAI Gazette, furthermore, teaches that the compounds of above formula (A) are serotonin $S_3$ (5-$HT_3$) receptor antagonists and are useful for therapeutic and prophylactic treatments of anorexia, nausea, emesis, abdominal fullness and the like accompanying acute and chronic gastritis, and such diseases as gastric and duodenal ulcer; or of nausea or emesis occurring with administration of anti-tumor agents, radioactive irradiation and motion sickness. The Gazette, however, is silent on their dopamine $D_2$ receptor antagonism.

Furthermore, WO93/08186 discloses a group of compounds represented by formula (B) below:

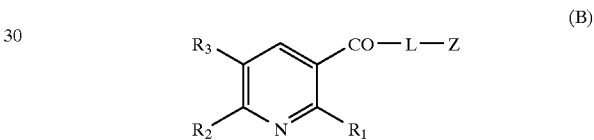

(B)

[in which $R_1$ stands for $C_{1-6}$ alkoxy, $C_{3-8}$ cycloalkoxy or $C_{3-8}$ cycloalkyl $C_{1-4}$ alkoxy; $R_2$ stands for hydrogen, halogen, $C_{1-6}$ alkyl, $C_{1-6}$ alkoxy, or amino which may be substituted with 1 or 2 $C_{1-6}$ alkyl; $R_3$ stands for hydrogen, halogen or $C_{1-6}$ alkyl; L is O or NH; and Z stands for di-azacyclic or azadicyclic side chain), teaching that said compounds are useful for therapeutic or prophylactic treatments of pain, emesis, central nervous system disorder and gastrointestinal disorder, as 5-$HT_3$ antagonists.

Said WO93/08186 cites, as one of adequate examples of di-azacyclic side chain Z. EP-A-358903 belonging to the patent family of afore-cited KOKAI Patent Application, KOKAI No. 92959/93, but contains no specific disclosure on a compound having a di-azacyclic side chain which is covered by the general formula (A) as above. Thus. WO93/08186 does not at all suggest the compound of the present invention.

On the other hand, domperidone [chemical name: 5-chloro-1-[1-[3-(2,3-dihydro-2-oxo-1H-benzimidazol-1-yl)propyl]-4-piperidinyl]-1,3-dihydro-2H-benzimidazol-2-one; cf. eg. Merck Index, 11th ed. 3412 (1989)] which is a dopamine $D_2$ receptor antagonistic agent, is effective to alleviate emesis accompanying various troubles of the digestive system and that accompanying infantile cold syndrome, but exhibits only insufficient effect on emesis occurring upon administration of anti-tumor agents such as cisplatin.

Recently, as a drug which can selectively and strongly inhibit the emesis occurring with administration of anti-tumor agents, serotonin $S_3$ receptor antagonistic agent has been developed, and currently such antiemetic agents as granisetron hydrochloride [chemical name: endo-1-methyl- N-(9-methyl-9-azobicyclo-[3.3.1]non-3-yl)-1H-indazole-3-carboxamide hydrochloride; cf. eg., Merck Index, 11th ed. 4443 (1989)], ondansetron hydrochloride (chemical name: 1,2,3,9-tetrahydro-9-methyl-3-[(2-methyl-1H-imidazol-1-yl)methyl]-4H-carbazol-4-one hydrochloride; cf. eg., Merck Index, 11th ed., 6802 (1989)] and azasetron hydrochloride [chemical name: (+)-N-1-azabicyclo-[2.2.2]oct-3-yl-6-chloro-3,4-dihydro-4-methyl-3-oxo-2H-1,4-benzoxazine-8-carboxamide hydrochloride; cf. eg., *Drugs of the Future*, 18(3), 206–211 (1993)] are clinically used. However, clinical application of these serotonin $S_3$ receptor antagonists is limited to the emesis mainly occurring in occasions of administration of anti-tumor agents. They furthermore are said to exhibit only insufficient effect on late emesis.

Thus, while drugs effective on specific type of emesis do exist, an antiemetic agent of wide application range which can strongly inhibit emesis induced by various causes has not yet been developed. Hence development of an antiemetic agent having a broad spectrum has been in demand.

DISCLOSURE OF INVENTION

In the process of our series of research work on potent and selective serotonin $S_3$ receptor antagonists, we have come to embrace a view that a substance which exhibits dopamine $D_2$ receptor antagonistic activity in addition to serotonin $S_3$ receptor antagonistic activity would be effective on emesis induced by various causes, and synthesized numbers of hexahydro-1H-1,4-diazepine derivatives with the view to impart dopamine $D_2$ receptor antagonistic activity to serotonin $S_3$ receptor antagonistic activity which hexahydro-1H-1,4-diazepine derivatives have, and conducted their screening. In consequence, it is now discovered that (R)-5-bromo-N-(1-ethyl-4-methylhexahydro-1H-1,4-diazepin-6-yl)-2-methoxy-6-methylamino-3-pyridinecarboxamide which is expressed by formula (I) below

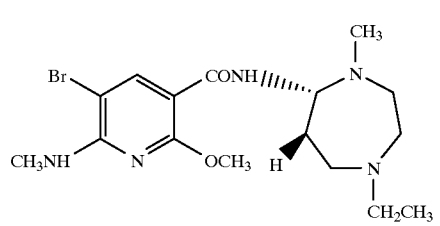

meets the object and possesses antiemetic effects of a broad spectrum.

Thus, the present invention provides (R)-5-bromo-N-(1-ethyl-4-methylhexahydro-1H-1,4-diazepin-6-yl)-2-methoxy-6-methylamino-3-pyridinecarboxamide of above formula (I), and its physiologically acceptable acid addition salts. The invention furthermore provides a method for preparing said compound. The invention also provides pharmaceutical preparations containing said compound. Still in addition, the invention provides an intermediate product for preparing said compound.

As physiologically acceptable acid addition salts of the compound of formula (I), for example, inorganic acid salts such as hydrochloride, hydrobromide, hydroiodide, sulfate and phosphate; and organic acid salts such as oxalate, maleate, fumarate, malonate, lactate, malate, citrate, tartarate, benzoate and methanesulfonate may be named.

The compound of formula (I) and physiologically acceptable acid addition salts thereof may be present in the form of hydrates and/or solvates, and these hydrates and/or solvates are also included in the compounds of the present invention.

The compound of the present invention can be prepared, for example, by reacting the compound of formula (II) below

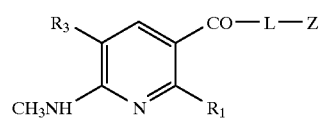

or a reactive derivative thereof with a compound of formula (III) below.

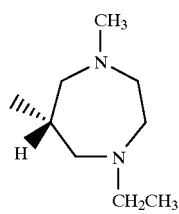

As reactive derivatives of the compound of formula (II), for example, lower alkyl esters (in particular, methyl ester), active esters, acid anhydrides, acid halides (in particular, acid chloride), etc. may be named. Specific examples of active ester include p-nitrophenyl ester, 2,4,5-trichlorophenyl ester and N-hydroxysuccinimide ester. As acid anhydrides, either of symmetric acid anhydrides and mixed acid anhydrides may be used. Specific examples of mixed acid anhydride include those with alkyl chloroformates such as ethyl chloroformate, isobutyl chloroformate and the like; those with aralkyl chloroformates such as benzyl chloroformate; those with aryl chloroformates such as phenyl chloroformate; and those with alkanoic acids such as isovaleric acid, pivalic acid, and the like.

When the compound per se of formula (II) is used as the starting material, the above reaction can be conducted in the presence of a condensing agent such as N,N'-dicyclohexylcarbodiimide, 1-ethyl-3-(3-dimethylamino-propyl)carbodiimide hydrochloride, N,N'-carbonyldiimidazole, N,N'-carbonyldisuccinimide, 1-ethoxycarbonyl-2-ethoxy-1,2-dihydroquinoline, dipenylphosphorylazide, propanephosphonic anhydride, benzotriazol-1-yloxy-tris(dimethylamino)phosphonium.hexafluorophosphate and the like.

The reaction of the compound of formula (II) or a reactive derivative thereof with the compound of formula (III) is conducted in the presence or absence of a solvent. Examples of useful solvent include aromatic hydrocarbons such as benzene, toluene and xylene; ethers such as diethyl ether, tetrahydrofuran and dioxane; halogenated hydrocarbons such as methylene chloride and chloroform; alcohols such as ethanol and isopropanol, ethyl acetate, acetone, acetonitrile, dimethylformamide, dimethylsulfoxide, ethylene glycol, water and the like. These solvents can be used each singly or in combination of more than one kind. If necessary, the reaction may be carried out in the presence of a base. Examples of the base useful in such an occasion include alkali hydroxide like sodium hydroxide and potassium hydroxide; alkali carbonate like sodium carbonate and potassium carbonate; alkali hydrogencarbonate like sodium hydrogencarbonate and potassium hydrogencarbonate; and organic base like triethylamine, tributylamine, diisopropyl-ethylamine and N-methylmorpholine. Suitable reaction temperatures normally are within a range from about −30° C. to about 200° C., preferably from about −10° C. to about 150° C. The compound of formula (III) can be supplied to the reaction system at a ratio of normally 1–3 moles, preferably 1–1.5 moles, per mole of the compound of formula (II) or a reactive derivative thereof. Whereas, it is also possible to use it in large excess if individual occasion demands, to let it function also as a base.

The compound of formula (II) to be used as the starting material can be prepared, for example, through the steps as indicated in Chart 1 below. Specific conditions for each of the steps are shown in later appearing Referential Example 1.

CHART 1

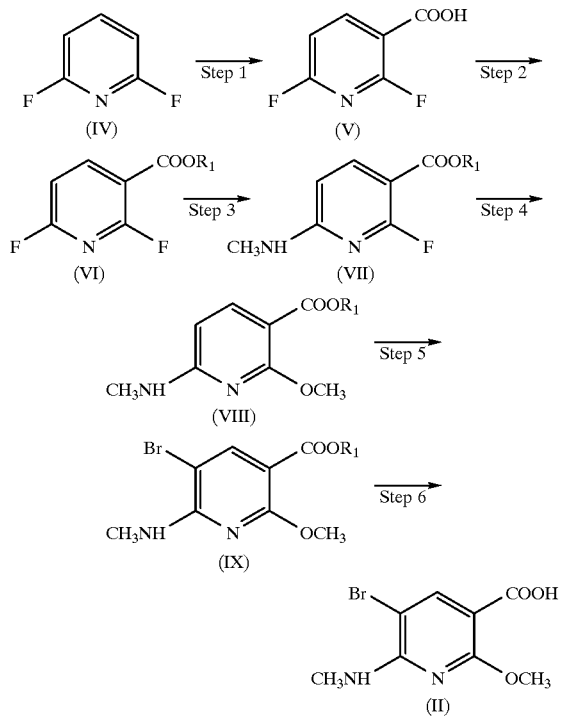

In the above formulae, $R_1$ stands for a linear or branched $C_1$–$C_6$ alkyl group.

The compound of formula (III) which is also used as the starting material is a novel compound not described in heretofore available literature and can be prepared, for example, through the steps indicated in Chart 2 below. Specific conditions for each of the steps are shown in later appearing Example 2.

CHART 2

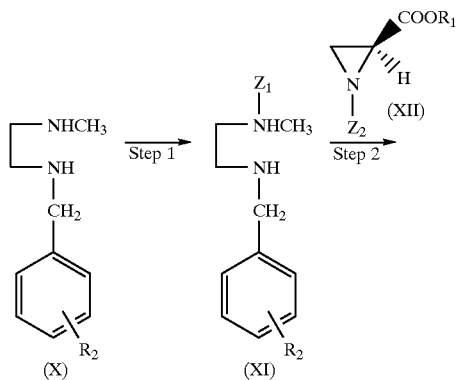

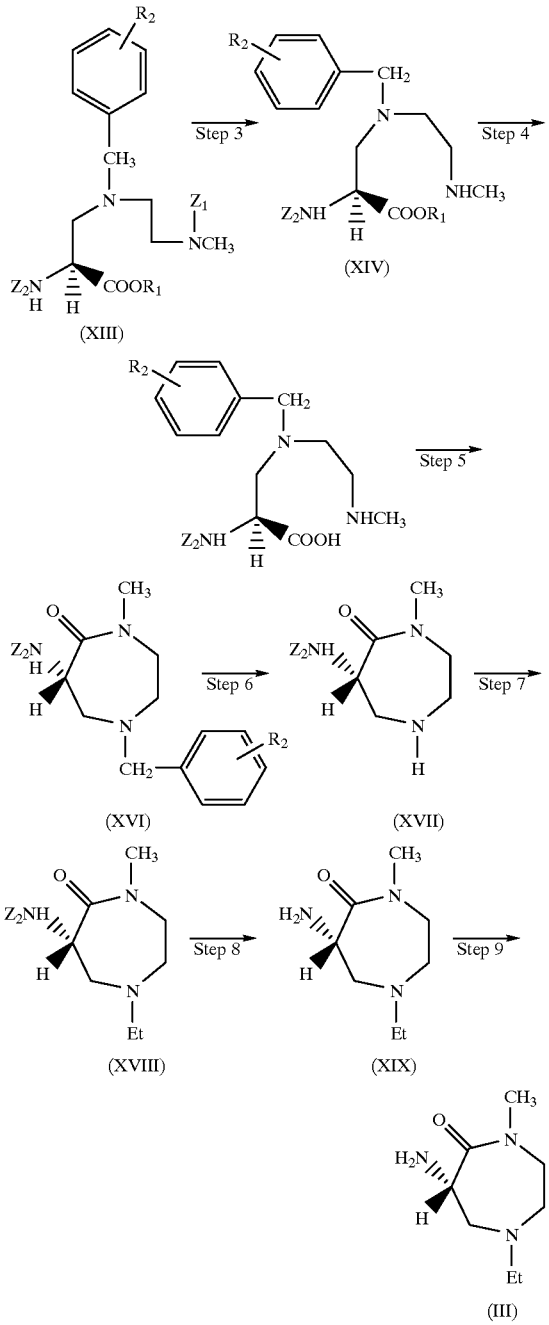

In the above formulae, Et stands for ethyl group; $Z_1$ stands for an amino-protecting group such as tert-butoxycarbonyl group, triphenylmethyl group and acetyl group; $Z_2$ stands for benzyloxycarbonyl group which is optionally substituted with chlorine atom, bromine atom, methoxy or nitro; $R_2$ stands for hydrogen atom, halogen atom, $C_{1-3}$ alkyl or $C_{1-3}$ alkoxy; and $R_1$ has the previously given signification.

The compound of above formula (III) may be obtained as an acid addition salt depending on the production method employed in individual occasions. As such, for example, earlier listed physiologically acceptable acid addition salts may be named. More specifically, inorganic acid salts such as hydrochloride, hydrobromide, hydroiodide, sulfate and phosphate; and organic acid salts such as oxalate, maleate, fumarate, malonate, lactate, malate, citrate, tartarate, benzoate and methanesulfonate may be named.

According to the above preparation method of the compound of formula (I), configuration of the compound of formula (III), one of the starting materials, is retained intact in the so produced compound of formula (I).

The compound of formula (I) as formed of the above preparation method can be isolated and purified by conventional techniques such as chromatography, recrystallization, reprecipitation or the like.

The compound of formula (I) and that of formula (III) may be obtained in the form of free base or acid addition salt depending on the reaction and processing conditions employed. The acid addition salt can be converted to a free base by conventional methods, eg., by a treatment with a base such as alkali carbonate and alkali hydroxide. Whereas, the free base can be led to an acid addition salt by a treatment with a desired acid according to conventional methods.

Hereinafter pharmacological test results of the compound of the invention and below-identified control compounds are presented to explain the pharmacological activities characteristic to the compound of this invention:

(1) Domperidone
   a selective dopamine $D_2$ receptor antagonist which has been clinically used as an antiemetic or gastrointestinal motility improving agent;
(2) Ondansetron Hydrochloride
   a selective serotonin $S_3$ receptor antagonist which has been clinically used as an antiemetic at the time of administering anti-tumor drug;
(3) Granisetron Hydrochloride
   a selective serotonin $S_3$ receptor antagonist which has been clinically used as an antiemetic at the time of administering anti-tumor drug;
(4) Metoclopramide Hydrochloride
   a drug which has been used world-wide as an antiemetic or gastrointestinal motility improving agent [chemical name: 4-amino-5-chloro-N-[2-(diethylamino)ethyl]-2-methoxybenzamide dihydrochloride monohydrate; cf. eg., Merck Index, 11th ed. 6063 (1989)].

A. On Dopamine $D_2$ Receptor- and Serotonin $S_3$ Receptor-Antagonistic Activities Test Example 1

Dopamine $D_2$ receptor-binding and serotonin $S_3$ receptor-binding activities (in vitro receptor binding assay)

Dopamine $D_2$ and serotonin $S_3$ receptor binding assays were carried out following the methods of I. Creese, et al. [*Eur. J. Pharmacol.*, 46, 337 (1977)] and S. J. Peroutka and A. Hamik [*Eur. J. Pharmacol.*, 148, 297 (1988)], respectively. Crude synaptosome fractions prepared from rat brain were used as receptor samples, and [$^3$H] spiperone ($D_2$) and [$^3$H] quipazine ($S_3$), as labelled ligands. A buffer solution containing each of the receptor sample and labelled ligand (final volume: 1 ml) was incubated for a prescribed period in the presence of one of the test compounds at various concentration levels, and thereafter the radioactive ligand bound to the receptor was isolated onto a filter using a cell-harvester (Brandel Co.) and radioactivity on each filter was measured with a liquid scintillation counter to determine the total amount bound to the receptor. Specifically bound amount was calculated by subtracting non-specifically bound amount from the total amount bound, said non-specifically bound amount being that bound under the presence of an excessive amount of non-labelled ligand [spiperone ($D_2$) and [$^3$H] quipazine ($S_3$)] which was concurrently measured. The concentration level of the test compound at which specific binding of labelled ligand was inhibited by 50% ($IC_{50}$ value) was calculated by probit analysis. The results are shown in Table 1.

Test Example 2

Inhibitory Effect on von Bezold-Jarisch Reflex (Antiserotonin $S_3$ Activity)

This test was carried out following the method of Fozard, et al. [cf. *Arch. Pharmacology*, 326, 36–44 (1984)]. Male Wister rats weighing 250–350 g were anesthetized with urethane (1.5 g/kg, intraperitoneal) and set on their backs. Electrocardiogram (lead II) and a heart rate on the animals were recorded on inkwriting oscillograph via a biophysical amplifier and pulse rate tachometer, respectively. When 2-methylserotonin (5-$HT_3$ agonist) of a dose of 10–30 μg/kg was administered intravenously, the heart rate was transiently decreased (von Bezold-Jarisch reflex). A fixed amount of 2-methylserotonin was repeatedly administered at 15-minute intervals until stable responses were obtained, and then a test compound was administered intravenously, 3 minutes before administration of 2-methylserotonin. The inhibition rate of von Bezold-Jarisch reflex after the administration of the test compound per the response before the administration was calculated, and the effective dose of the test compound to cause 50% inhibition ($ED_{50}$ value) was determined by probit analysis. The result was as shown in Table 1 below.

TABLE 1

| Test Compound | Test Example 1 $IC_{50}$ (nM) | | Test Example 2 $ED_{50}$ (μg/kg) von Bezold-Jarisch Reflex Inhibition |
|---|---|---|---|
| | $D_2$ | $S_3$ | |
| Compound of Example 1 | 11.7 | 1.0 | 1.9 |
| domperidone | 14 | >1000 | >10000 |
| ondansetron hydrochloride | >100000 | 4.2 | 1.1 |
| granisetron hydrochloride | >100000 | 2.0 | 0.26 |
| metoclopramide hydrochloride | 630 | 880 | 181 |

As is clear from the results indicated in above Table 1, the compound of Example 1 exhibited more than equivalent dopamine $D_2$ receptor binding activity to that of domperidone which is a known selective dopamine $D_2$ receptor antagonist, as well as strong serotonin $S_3$ receptor binding activity excelling over those of ondansetron hydrochloride and granisetron hydrochloride which are known selective serotonin $S_3$ receptor antagonists. Also for von Bezold-Jarisch reflex inhibition, the compound of the invention has excellent effect comparable to that of ondansetron hydrochloride. As an antiemetic agent exhibiting binding activity to both serotonin $S_3$ and dopamine $D_2$ receptors, metoclopramide hydrochloride is known. However, its binding activity to the two receptors is far weaker than that of the compound of Example 1.

Thus, the compound of the invention has potent antagonistic activities to both serotonin $S_3$ and dopamine $D_2$ receptors, and is a highly promising antiemetic agent of a broad spectrum to inhibit emesis inducted by various causes.

B. On Antiemetic Effects

Test Example 3

Inhibitory Effect on Apomorphine-induced Emesis

Three to four Beagle dogs (body weight: 8–15 kg) per group were used to examine the inhibitory effect of the test compounds on apomorphine-induced emesis. This test has been commonly conducted as a method for detecting dopamine blocker. Each of the test animals was orally administered with a prescribed dose of a test compound as dissolved or suspended in 0.5% tragacanth solution, and two hours thereafter, was administered with apomorphine hydrochloride (0.3 mg/kg) by subcutaneous injection at the back.

The number of emetic episodes induced within the following 1 hour was counted, and the inhibition rate was calculated by comparing the number of emetic episodes of the tested group of dogs with that of the control group, and the effective dose of each test compound for inhibiting the emesis by 50% ($ED_{50}$ value) was determined by probit analysis. The result was as shown in Table 2.

Test Example 4

Effect on Cisplatin-induced Emesis in Ferrets

Male ferrets (Marshall Lab., U.S.A.) weighing approximately 1 kg were used. For intravenous injection, a cannule was implanted in the cervical vein under pentobarbital anethesia, 3–4 days in advance of the experiment. To each test group each a prescribed dose of a test compound as dissolved or suspended in 0.5% tragacanth solution was orally administered, and 30 minutes thereafter, cisplatin (Sigma) 10 mg/kg (physiological salt solution, 3 ml/kg) was administered intravenously through the cannule. The number of emetic episodes induced within the following 3 hours was recorded and the inhibition rate of the test compound was calculated. The effective doses of the test compounds to inhibit the emesis by 50% ($ED_{50}$ values) as determined by probit analysis were as indicated in Table 2.

Test Example 5

Effect on Cisplatin-induced Emesis in Dog

Four to five Beagle dogs (body weight: 10–12 kg) per group were used to examine the inhibitory effect of the test compounds on cisplatin-induced emesis. To each test group each a prescribed dose of a test compound as dissolved or suspended in 0.5% tragacanth solution was orally administered, and 30 minutes thereafter, cisplatin (Sigma) 3 mg/kg (physiological salt solution, 3 ml/kg) was intravenously administered. The number of emetic episodes within the 5 hours following the cisplatin administration was recorded to calculate the inhibition rate of each test compounds, and the effective dose ($ED_{50}$ value) for inibiting the emesis by 50% was determined by probit analysis. The results were as indicated in Table 2 below.

TABLE 2

| Test Compound | Test Example 3 Apomorphine-induced emesis dog $ED_{50}$, mg/kg | Test Example 4 Cisplatin-induced emesis ferret $ED_{50}$, mg/kg | Test Example 5 Cisplatin-induced emesis dog $ED_{50}$, mg/kg |
| --- | --- | --- | --- |
| Compound of Example 1 | 0.19 | 0.03 | 0.29 |
| domperidone | 0.02 | >10 | >3 |
| ondansetron hydrochloride | >10 | 0.1 | 0.16 |
| metoclopramide hydrochloride | 0.45 | 0.98 | 3.96 |

As is clear from the results shown in Table 2, the compound of Example 1 exhibited excellent inhibitory effect on apomorphine-induced emesis based on its dopamine $D_2$ receptor antagonism with certainty, although it's effect is not equal to that of domperidone which is a selective dopamine $D_2$ receptor antagonist. Moreover, as a specially remarkable effect, the compound exhibited strong inhibiting effect on cisplatin-induced emesis based on its serotonin $S_3$ receptor antagonism, of approximately equivalent level to that of ondansetron hydrochloride which is a selective serotonin $S_3$ receptor antagonist. Those results suggest that the compound of Example 1 possesses a broad spectrum of antiemetic effect, due to its excellent property concurrently exhibiting potent serotonin $S_3$ and dopamine $D_2$ receptor antagonistic activities in good balance.

The compound of Example 1, furthermore, exhibited stronger antiemetic effect than metoclopramide hydrochloride which has weak binding activity to both of serotonin $S_3$ and Dopamine $D_2$ receptors. In particular, it exhibited far stronger inhibitory effect on cisplatin-induced emesis, clearly showing significant difference in effect from metoclopramide hydrochloride.

C. On the Effect on Central System

Test Example 6

Inhibitory Effect on Exploratory Activity

Male mice (5 per group, Std-ddy strain, weighing 20–25 g) were used as the test animals, each of which was orally administered with a test compound which was dissolved or suspended in 0.5% tragacanth solution and after 2 hours from the administration put in a test cage (23×35×30 cm) on Animex activity meter (Farad Co.). Exploratory activity of each mouse was counted for the following 3 minutes. The mean counts of exploratory activities (count/3 min.) per group of the tested mice was compared with that of the control group to calculate the inhibition rate, and the effective dose ($ED_{50}$ value) of each test compound for 50% inhibition was determined by probit analysis.

The $ED_{50}$ values of the compound of Example 1 and metoclopramide hydrochloride were 48.5 mg/kg and 22.4 mg/kg, respectively, indicating that the former has weaker central inhibitory effect.

As is clear from the foregoing test results, the compound of formula (I) and physiologically acceptable acid addition salts thereof exhibit excellent antiemetic effects based on its potent serotonin $S_3$ receptor and dopamine $D_2$ receptor antagonistic activities, and are useful for treatment or prophylaxis of various gastrointestinal symptoms which are associated with various diseases and drug administration, as antiemetic agents of broad spectrum. More specifically, they are useful for treatment or prophylaxis of nausea, emesis, anorexia, abdominal fullness, upper abdominal discomfort, abdominal pain, heartburn, eructation and the like which are apt to accompany such diseases as acute and chronic gastritis, esophageal reflux, gastric and duodenal ulcer, gastric neurosis, gastroptosis, postgastrectomy syndrome, scleroderma, diabetes, esophageal and biliary duct disorders, puerile periodic vomiting and upper respiratory tract infections. They are also useful for treatment and prophylaxis of, for example, irritable bowel syndrome, constipation and infant diarrhea. Furthermore, they can be used for treatment or prophylaxis of nausia or emesis induced by administration of anti-tumor agents or levodopa preparations, or morphine which is a narcotic analgesic, or at the time of radioactive irradiation. Still more, they can be used for treatment or prophylaxis of intoxication with addictive drug (morphine, nicotine, amphetamine, and the like), as an anti-psychotic or anxiolytic agent.

The compound of formula (I) and physiologically acceptable acid addition salts thereof can be administered orally, non-parenterally or intrarectally. While the clinical dose varies with such factors as kind of the compound, administration route, severity of the disease and age of the patient, when it is used as an antiemetic, for example, normally an adequate dose range is 0.01–10 mg/kg/day, preferably 0.1–3 mg/kg/day. When it is used as an anti-psychotic agent, an adequate dose range is normally 3–50 mg/kg/day, preferably 5–30 mg/kg/day.

For applying the compound of formula (I) or physiologically acceptable acid addition salts thereof to the medical uses as above, they are normally administered in the form of preparations formulated by mixing with known carriers for pharmaceutical preparations. As the carriers, those customarily used in the field of medical preparations which are non-reactive with the compound of the present invention and non-toxic are used. Specific examples of such carriers include citric acid, glutamic acid, glycine, lactose, inositol, glucose, mannitol, dextran, sorbitol, cyclodextrin, starch, partly pregelatinized starch, sucrose, methyl p-hydroxybenzoate, propyl p-hydroxybenzoate, magnesium aluminometasilicate, synthetic aluminium silicate, crystalline cellulose, carboxymethyl cellulose sodium, hydroxypropyl starch, carboxymethyl cellulose calcium, ion-exchange resins, methyl cellulose, gelatin, gum arabic, pullulan, hydroxypropyl cellulose, lowly substituted hydroxypropyl cellulose, hydroxypropylmethyl cellulose, polyvinylpyrrolidone, polyvinyl alcohol, alginic acid, sodium alginate, light silicic anhydride, magnesium stearate, talc, tragacanth, bentonite, veegum, carboxyvinyl polymer, titanium dioxide, sorbitan fatty acid ester, sodium laurylsulfate, glycerin, fatty acid glycerides, purified lanolin, glycerogelatin, polysorbate, macrogol, vegetable oil, wax, propylene glycol, ethanol, benzyl alcohol, sodium chloride, sodium hydroxide, hydrochloric acid and water.

As applicable preparation forms, tablet, capsule, granule, powder, syrup, suspension, injection and suppository may be named. These preparations can be prepared following known and conventional methods. Liquid preparations may take a form which is dissolved or suspended in water or other suitable media immediately before administration. Tablets and granules may be coated by a method well known per se.

These preparations can contain at least 0.01%, preferably 0.1–70%, of the compound of formula (I) or a physiologically acceptable acid addition salt thereof. These preparations may further contain therapeutically useful other component(s).

Hereinafter the present invention is explained still more specifically, referring to Referential Examples and working Examples, it being understood that the invention is in no way limited by these Examples. Identification of the formed compounds was conducted by such means as elemental analysis, mass spectrum, IR spectrum and NMR spectrum.

In the following Referential Examples and working Examples, the following abbreviations may be used for simplifying the disclosures:
J: coupling constant
s: singlet
d: doublet
t: triplet
m: multiplet
br-s: broad singlet
ee: enantiometric excess

REFERENTIAL EXAMPLE 1

Preparation of 5-bromo-2-methoxy-6-methylamino-3-pyridinecarboxylic Acid (1) Fifty (50) g of 2,6-difluoropyridine was dissolved in 200 ml of tetrahydrofuran, and into the solution 326 ml of 1.6M n-butyl lithium-tetrahydrofuran solution was added dropwise at −70° C., followed by an hour's stirring at the same temperature. To the reaction mixture 29 g of dry ice blocks were added little by little, followed by 30 minutes' stirring at the same temperature. Raising the temperature to about 5° C., 500 ml of ice water was added. The reaction mixture was washed twice with ethyl acetate, and the aqueous layer was adjusted to pH 3 with conc. hydrochloric acid. The aqueous layer was then extracted with chloroform. The extract was washed with saturated saline water, dried over anhydrous magnesium sulfate, and the solvent was concentrated under reduced pressure. The crystalline precipitate was collected by filtration, and recrystallized from diethyl ether-n-hexane to provide 63 g of 2,6-difluoro-3-pyridinecarboxylic acid (m.p. 170–171° C.).

(2) A mixture of 63 g of above product, 700 ml of methanol and 5 ml of conc. sulfuric acid was heated under reflux for 20 hours. After evaporating the solvent under reduced pressure, the residue was diluted with ice water and extracted with chloroform. The extract was washed with water, dried over anhydrous magnesium sulfate, and the solvent was evaporated under reduced pressure. The residue was subjected to silica gel column chromatography, eluted with chloroform and purified to provide 64 g of methyl 2,6-difluoro-3-pyridinecarboxylate as an oil.

(3) To 500 ml of ethanol solution containing 38 g of above product, 72 g of 20% methylamine solution in ethanol was added dropwise at −20° C. to −25° C. The mixture was stirred for 5 hours at the same temperature which was subsequently raised to room temperature. The reaction mixture was concentrated under reduced pressure. To the condensate ice water was added, and the precipitates were collected by filtration, washed with water, dried and recrystallized from diethyl ether-n-hexane (2:3). Thus, 15.7 g of methyl 2-fluoro-6-methylamino-3-pyridinecarboxylate (m.p. 156–159° C.) was obtained.

(4) To 400 ml of a methanol solution containing 15.7 g of above product, 19.1 g of potassium tert.butoxide was added and heated under reflux for 3 hours. After cooling, the reaction mixture was concentrated under reduced pressure, and aqueous sodium hydrogen-carbonate solution was added to the residue. Then the precipitate was collected by filtration, washed with water and dried to provide 16.3 g of methyl 2-methoxy-6-methylamino-3-pyridinecarboxylate (m.p. 120–122° C., as recrystallized from n-hexane-diethyl ether).

(5) To 70 ml of a dimethylformamide solution containing 7.3 g of above product, 7.0 g of N-bromosuccinimide was added and heated at 80° C. for 4 hours. Ice water was added to the reaction liquid and whereby precipitate was collected by filtration, washed with water and dried to provide 9.8 g of methyl 5-bromo-2-methoxy-6-methylamino-3-pyridinecarboxylate (m.p. 136–138° C., as recrystallized from n-hexane-diethyl ether).

(6) To 100 ml of a methanol solution containing 20 g of above product, 200 ml of an aqueous solution containing 3.1 g of sodium hydroxide was added, followed by 1.5 hours' heating under reflux. After cooling, methanol was evaporated under reduced pressure, and the residue was acidified with conc. hydrochloric acid. The solid thus precipitated was collected by filtration, washed with water and dried to provide 18.9 g of the object product (m.p. 224–225° C.).

$^1$H-NMR spectrum (DMSO-$d_6$, δ ppm): 2.92 (3H, d, J=5 Hz), 3.88 (3H, s), 7.08 (1H, d, J=5 Hz), 7.98 (1H, s), 12.08 (1H, s)

EXAMPLE 1

Preparation of (R)-5-bromo-N-(1-ethyl-4-methylhexahydro-1H-1,4-diazepin-6-yl)-2-methoxy-6-methylamino-3-pyridinecarboxamide Difumarate (1) A liquid mixture of 18.0 g of 5-bromo-2-methoxy-6-methylamino-3-pyridinecarboxylic acid, 11.7 g of N,N'-carbonyldiimidazole and 50 ml of dimethylformamide was stirred for at room temperature 8 hours. To the reaction mixture then 13.0 g of (R)-6-amino-1-ethyl-4- methylhexahydro-1H-1,4-diazepine was added, followed by 15 hours' stirring at room temperature. The reaction mixture was concentrated under reduced pressure, and to which an aqueous 2N sodium hydroxide solution was added, followed by extraction with chloroform. The extract was washed with water, dried over anhydrous magnesium sulfate, and the solvent was evaporated under reduced pressure. The residue was subjected to silica gel column chromatography, eluted and purified with chloroform-methanol (15:1) and recrystallized from diethyl ether to provide 19.6 g of (R)-5-bromo-N-(1-ethyl-4-methylhexahydro- 1H-1,4-diazepin-6-yl)-2-methoxy-6-methylamino-3-pyridinecarboxamide ¼ hydrate (m.p. 52–55° C.).

This compound showed a retention time of 23.6 minutes in high performance liquid chromatography (HPLC) conducted under the below-specified conditions, and had an optical purity of at least 99% ee.

HPLC Conditions

HPLC column: CHIRALPAK AS (Daicel Chemical Industries)

inner diameter 4.6 mm×250 mm mobile phase: n-hexane-ethanol-diethylamine (940:30:2)

flow rate: 0.8 ml/min.

temp.: 25° C.

detection: UV 254 nm (2) Nineteen (19) g of above product was treated with fumaric acid to be converted to difumarate, and recrystallized from ethanol to provide 23 g of the object product (m.p. 152–155° C.).

$^1$H-NMR spectrum (DMSO-d$_6$, δ ppm): 1.02 (3H, t, J=7 Hz), 2.43 (3H, s), 2.5–3.0 (10H, m), 2.93 (3H, d, J=5 Hz), 3.98 (3H, s), 4.14 (1H, m), 6.60 (4H, s), 6.99 (1H, d, J=5 Hz), 8.09 (1H, s), 8.48 (1H, d, J=8 Hz), 12.80 (2H, br-s)

REFERENTIAL EXAMPLE 2

Preparation of (S)-5-bromo-N-(1-ethyl-4-methylhexahydro-1H-1,4-diazepein-6-yl)-2-methoxy-6-methylamino-3-pyridinecarboxamide Difumarate (1) The reaction and processing in Example 1 (1) were repeated except that (R)-6-amino-1-ethyl-4-methylhexahydro-1H-1,4-diazepine was replaced with (S)-6-amino-1-ethyl-4-methylhexahydro-1H-1,4-diazepine, and (S)-5-bromo-N-(1-ethyl-4-methylhexahydro-1H-1,4-diazepin-6-yl)-2-methoxy-6-methylamino-3-pyridinecarboxamide monohydrate was obtained (m.p. 67–68° C., as recrystallized from diethyl ether-petroleum ether).

Said compound showed a retention time of 27.5 minutes in HPLC under the same conditions as those indicated in Example 1, and had an optical purity of at least 99% ee.

(2) The above-formed product was treated with fumaric acid and converted to difumarate, which was recrystallized from ethanol to provide the object product (m.p. 152–155° C.).

EXAMPLE 2

Preparation of (R)-6-amino-1-ethyl-4-methylhexahydro-1H-1,4-diazepine (1) To a mixture of 1200 ml of chloroform and 1602 g of N'-methyl-N-(3-methylbenzyl)ethylenediamine, a mixture of 3500 ml of a chloroform solution and 2180 g of di-tert-butyl dicarbonate was added dropwise under cooling with ice. After stirring the reaction mixture then for 18 hours at room temperature, the reaction mixture was concentrated to dryness under reduced pressure. Adding toluene and ice water to the residue, 10% aqueous citric acid solution was added dropwise thereto under cooling with ice to maintain the temperature inside the solution at not higher than 4° C. Whereupon the aqueous layer was made acidic. The toluene layer was separated and extracted with water. Thus obtained aqueous layer was combined with the acidic aqueous solution, and washed with toluene. The aqueous layer was made alkaline with 48% aqueous sodium hydroxide solution and reextracted with toluene. The extract was washed with water and saturated saline solution and dried over anhydrous sodium sulfate. Evaporating the solvent under reduced pressure, 1860 g of N'-tert.butoxycarbonyl-N'-methyl-N-(3-methylbenzyl)ethylenediamine was obtained as an oily product.

(2) Fifty (50) g of above product was mixed with 53 g of (S)-2-methoxycarbonyl-1-benzyloxycarbonylaziridine and stirred at 80° C. for 20 hours. Whereupon rude methyl (R)-2-(benzyloxycarbonyl)amino-3-[N-[2[N'-(tert-butoxycarbonyl)-N'-methylamino]ethyl]-N-(3-methylbenzyl)]aminopropionate was obtained.

(3) To the above crude product, 750 ml of 10% hydrogen chloride in ethanol solution was added and stirred for 2 hours at 30–40° C. Insoluble materials were removed by filtration, solvent was evaporated under reduced pressure, and the residue was dissolved in 500 ml of water. The aqueous layer was washed with diethyl ether, neutralized with sodium hydrogencarbonate and extracted with chloroform. The extract was dried over anhydrous magnesium sulfate, and the solvent was evaporated under reduced pressure to provide 79 g of crude methyl (R)-2-(benzyloxycarbonyl)amino-3-[N-(2-methylaminoethyl)-N-(3-methylbenzyl)]aminopropionate. A part of the product was converted to a form of the corresponding oxalate which was recrystallized from ethanol-diethyl ether to provide an oxalate of said methyl ester: m.p. 185–190° C.

(4) Thirty-nine (39) g of above crude methyl ester was dissolved in 70 ml of ethanol, and into which 70 ml of aqueous 2N sodium hydroxide solution was added dropwise at 0° C.–10° C., followed by 16 hours' stirring at room temperature. Evaporating the ethanol under reduced pressure, the aqueous solution was adjusted to pH 8 with conc. hydrochloric acid and extracted with chloroform. The extract was dried over anhydrous magnesium sulfate and the solvent was evaporated under reduced pressure, to provide 36.4 g of crude (R)-2-(benzyloxycarbonyl)mino-3-[N-(2-methylaminoethyl)-N-(3-methylbeznyl)]aminopropionic acid. A part of the product was purified to provide a crystalline product having melting point at 170–175° C.

(5) To a solution of 36.4 g of above crude product in 180 ml of methylene chloride, 18.2 g of 1-ethyl- 3-(3-dimethylaminopropyl)carbodiimide hydrochloride was added, followed by 20 hours' stirring at room temperature. The reaction mixture was washed with water, dried over anhydrous magnesium sulfate, the solvent was evaporated under reduced pressure, and the residue was recrystallized from diethyl ether-n-hexane to provide 22 g of (S)-3-(benzyloxycarbonyl)amino-1-methyl-4-(3-methylbenzyl) hexahydro-2-oxo-1,4-diazepine (m.p. 70–71° C.).

(6) To a mixture of 400 ml of methylene chloride and 40.8 g of above product, 18.0 g of 1-chloroethyl chloroformate was added dropwise, followed by 3 hours' stirring at room temperature. The solvent was evaporated under reduced pressure, and 400 ml of methanol was added to the residue, followed by an hour's heating under reflux. Evaporating the methanol under reduced pressure, water was added to the residue which was subsequently washed with diethyl ether. The aqueous layer was made alkaline with aqueous sodium hydroxide solution and extracted with chloroform. The extract was dried over anhydrous magnesium sulfate and the solvent therein was evaporated under reduced pressure to provide crude (S)-3-(benzyloxycarbonyl)amino-1-methylhexahydro-2-oxo-1,4-diazepine.

(7) To the above crude product 600 ml of methanol and 21.2 g of triethylamine were added, and further 11.6 g of 80% aqueous acetaldehyde solution was added under cooling with ice, followed by 2 hours' stirring. Then 3.97 g of sodium borohydride was added portionwise at the same temperature, and the mixture was stirred for an hour under cooling with ice and for subsequent 16 hours at room temperature. After evaporating the solvent under reduced pressure, the residue was extracted with chloroform. The extract was washed with saturated saline water, dried over anhydrous magnesium sulfate and the solvent was evaporated under reduced pressure. The residue was subjected to silica gel column chromatography, eluted and purified with chloro-form-methanol (15:1) to provide 28 g of (S)-3-(benzyloxycarbonyl)amino-5-ethyl-1-methylhexahydro-2-oxo-1,4-diazepine as an oil.

(8) To 28 g of the above product 140 ml of 48% aqueous hydrobromic acid solution was added, followed by 2 hours' heating under stirring at 60° C. After cooling, the reaction mixture was washed with diethyl ether twice, and the aqueous layer was made alkaline with potassium carbonate and extracted with chloroform. The extract was dried over anhydrous magnesium sulfate. Evaporating the solvent under reduced pressure, 19 g of (S)-3-amino-5-ethyl-1-methylhexahydro-2-oxo-1,4-diazepine was obtained as an oily product.

(9) To 300 ml of a tetrahydrofuran solution containing 23 g of the above product, 1000 ml of 1M borane-tetrahydrofuran solution was added dropwise, followed by 16 hours' stirring at room temperature. Then 500 ml of 1N hydrochloric acid was added under cooling with ice, and the mixture was heated for an hour under reflux. After cooling the mixture, the solvent was evaporated under reduced pressure, and the residue was washed twice with diethyl ether and the aqueous layer was made alkaline with potassium carbonate and extracted with chloroform. The extract was dried over anhydrous magnesium sulfate. Evaporating the solvent under reduced pressure, 19 g of the object product was obtained as an oil.

REFERENTIAL EXAMPLE 3

Preparation of (S)-6-amino-1-ethyl-4-methylhexahydro-1H-1,4-diazepine

The object compound was obtained by carrying out the reactions and processing in the similar manner to those of Example 2 (2)–(9), except that (S)-2-methoxycarbonyl-1-benzyloxycarbonylaziridine used in the Step (2) was replaced with (R)-2-methoxycarbonyl-1-benzyloxycarbonylaziridine.

FORMULATION EXAMPLE 1

| Preparation of tablets (5 mg tablet) | |
|---|---|
| (R)-5-bromo-N-(1-ethyl-4-methylhexahydro-1H-1,4-diazepin-6-yl)-2-methoxy-6-methylamino-3-pyridinecarboxamide difumarate | 5 g |
| Lactose | 80 g |
| Corn starch | 30 g |
| Crystalline cellulose | 25 g |
| Hydroxypropylcellulose | 3 g |

| Preparation of tablets (5 mg tablet) -continued | |
|---|---|
| Light silicic anhydride | 0.7 g |
| Magnesium stearate | 1.3 g |

Following the conventional manner, the above components were mixed, granulated and punched into 1,000 tablets each weighing 145 mg.

FORMULATION EXAMPLE 2

| Preparation of powder (1% powder) | |
|---|---|
| (R)-5-bromo-N-(1-ethyl-4-methylhexahydro-1H-1,4-diazepin-6-yl)-2-methoxy-6-methylamino-3-pyridinecarboxamide difumarate | 10 g |
| Lactose | 960 g |
| Hydroxypropylcellulose | 25 g |
| Light silicic anhydride | 5 g |

Following the conventional manner, the above components were mixed and processed into a powder preparation.

FORMULATION EXAMPLE 3

| Preparation of injection (0.5% injection) | |
|---|---|
| (R)-5-bromo-N-(1-ethyl-4-methylhexahydro-1H-1,4-diazepin-6-yl)-2-methoxy-6-methylamino-3-pyridinecarboxamide difumarate | 10 g |
| Sorbitol | 100 g |
| Water for injection | a suitable amount |
| Total | 2,000 ml |

(R)-5-bromo-N-(1-ethyl-4-methylhexahydro-1H-1,4-diazepin-6-yl)-2-methoxy-6-methylamino-3-pyridinecarboxamide difumarate and sorbitol were dissolved in a part of the water for injection, and then the remainder of the injection liquid was added to make the total amount 2,000 ml. This solution was filtered through a membrane filter (0.22 μm). The filtrate was filled in 2 ml ampoules and sterilized at 121° C. for 20 minutes.

INDUSTRIAL APPLICABILITY

As explained above, the compound of the present invention as represented by formula (I) and its physiologically acceptable acid addition salts exhibit excellent antiemetic effect based on their potent serotonin $S_3$ and dopamine $D_2$ receptor antagonistic activities, and are useful as an antiemetic agent for treatment or prophylaxis of various gastrointestinal symptoms which are associated with various diseases and drug administration. More specifically, they are useful for treatment or prophylaxis of nausea, emesis, anorexia, abdominal fullness, upper abdominal discomfort, abdominal pain, heartburn, eructation and the like which are apt to accompany such diseases as acute and chronic gastritis, esophageal reflux, gastric and duodenal ulcer, gastric neurosis, gastroptosis, postgastrectomy syndrome, scleroderma, diabetes, esophageal and biliary duct disorders, puerile periodic vomiting and upper respiratory tract infections. They are also useful for treatment and prophylaxis of, for example, irritable bowel syndrome, constipation and infant diarrhea. Furthermore, they can be used for treatment or prophylaxis of nausia or emesis induced by administra-

We claim:

1. (R)-5-bromo-N-(1-ethyl-4-methylhexahydro-1H-1,4-diazepin-6-yl)-2-methoxy-6-methylamino-3-pyridinecarboxamide which is expressed by formula (I) below

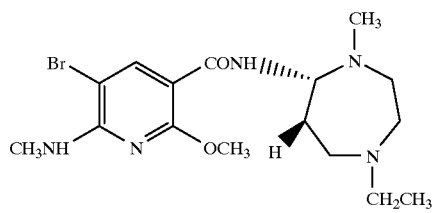

or physiologically acceptable acid addition salts thereof.

2. A method for preparation of a compound of claim 1 which comprises reacting a compound of formula

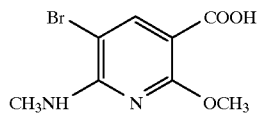

or a reactive derivative thereof with a compound of formula (III) below

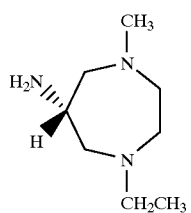

and if necessary, converting the resulting product in the form of the free base to a corresponding physiologically acceptable acid addition salt.

3. A unit dosage form of a medicament containing the compound of formula (I) as set forth in claim 1 or a physiologically acceptable acid addition salt thereof.

4. A pharmaceutical composition which comprises the compound of formula (I) as set forth in claim 1 or a physiologically acceptable acid addition salt thereof, and a carrier for medical preparations.

5. A method for treatment of or Prophylaxis against nausea or emesis which comprises administering an effective amount of the compound of formula (I) as set forth in claim 1 or a physiologically acceptable acid addition salt thereof to a patient suffering from nausea or emesis.

* * * * *

UNITED STATES PATENT AND TRADEMARK OFFICE
CERTIFICATE OF CORRECTION

PATENT NO. : 5,945,415
DATED : August 31, 1999
INVENTOR(S) : Shiro KATO et al.

It is certified that error appears in the above-indentified patent and that said Letters Patent is hereby corrected as shown below:

Title page,

Column 2, in the ABSTRACT, correct the formula to read:

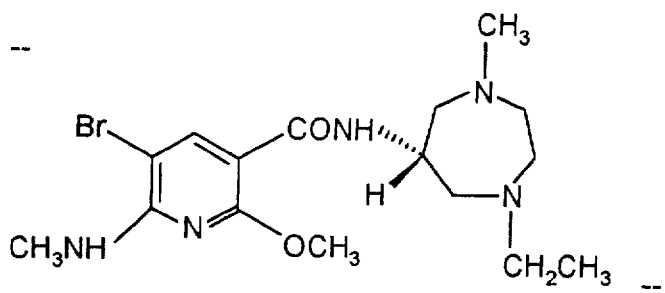

Column 3, line 7, change "(+)" to --(±)--;

lines 35-45, correct the formula to read:

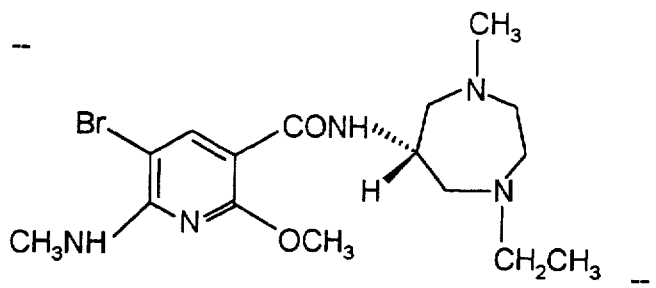

UNITED STATES PATENT AND TRADEMARK OFFICE
CERTIFICATE OF CORRECTION

PATENT NO. : 5,945,415
DATED : August 31, 1999
INVENTOR(S) : Shiro KATO et al.

It is certified that error appears in the above-indentified patent and that said Letters Patent is hereby corrected as shown below:

Column 4, lines 4-10, rewrite entirely to read:

--

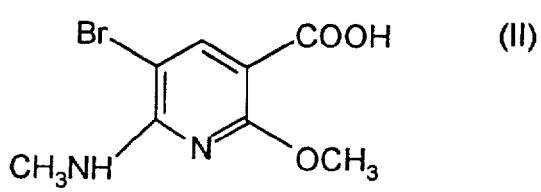

(II)

-- and lines 15-24, correct the formula to read:

--

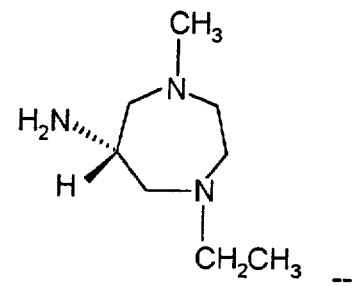

--

UNITED STATES PATENT AND TRADEMARK OFFICE
CERTIFICATE OF CORRECTION

PATENT NO. : 5,945,415
DATED : August 31, 1999
INVENTOR(S) : Shiro KATO et al.

It is certified that error appears in the above-indentified patent and that said Letters Patent is hereby corrected as shown below:

Column 17, claim 1, correct formula (I) to read:

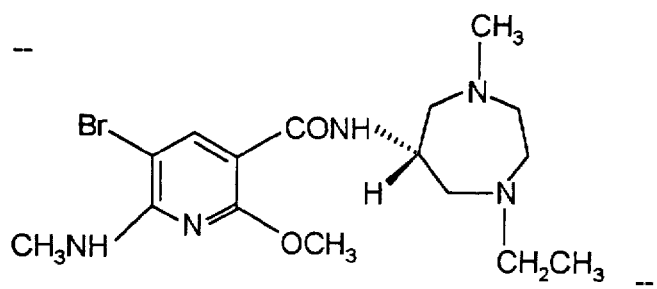

Column 18, claim 5, line 1, change "Prophylaxis" to --prophylaxis--.

Signed and Sealed this

Ninth Day of May, 2000

*Attest:*

Q. TODD DICKINSON

*Attesting Officer*   *Director of Patents and Trademarks*